United States Patent
Finch et al.

(10) Patent No.: US 9,504,253 B2
(45) Date of Patent: Nov. 29, 2016

(54) LIQUID PESTICIDE COMPOSITION CONTAINING N-PHENYLSEMICARBAZONE PESTICIDE COMPOUNDS

(75) Inventors: Charles W. Finch, Garner, NC (US); William M. Fletcher, Bahama, NC (US); Monica Walker, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 838 days.

(21) Appl. No.: 12/443,202

(22) PCT Filed: Oct. 2, 2007

(86) PCT No.: PCT/EP2007/060449
§ 371 (c)(1),
(2), (4) Date: Mar. 27, 2009

(87) PCT Pub. No.: WO2008/040727
PCT Pub. Date: Apr. 10, 2008

(65) Prior Publication Data
US 2009/0317433 A1    Dec. 24, 2009

Related U.S. Application Data

(60) Provisional application No. 60/849,145, filed on Oct. 3, 2006.

(30) Foreign Application Priority Data

Nov. 8, 2006    (EP) .................................... 06123698

(51) Int. Cl.
*A01N 47/34*    (2006.01)

(52) U.S. Cl.
CPC ..................... *A01N 47/34* (2013.01)

(58) Field of Classification Search
CPC ...... A01N 47/34; A01N 37/44; A01N 47/44; A01N 25/14; A01N 59/00
See application file for complete search history.

(56) References Cited

U.S. PATENT DOCUMENTS

2008/0213326 A1    9/2008 Amrhein et al.

FOREIGN PATENT DOCUMENTS

| EP | 0462456 | 12/1991 |
|---|---|---|
| JP | 2007297316 | 11/2007 |
| WO | 88/07326 | 10/1988 |
| WO | 90/03112 | 4/1990 |
| WO | 2006/002984 | 1/2006 |
| WO | 2006/015791 | 2/2006 |

OTHER PUBLICATIONS

International Preliminary Report on Patentability dated Feb. 2, 2009 from corresponding International Application No. PCT/EP2007/060449, filed Oct. 2, 2007.
International Search Report completed Jul. 28, 2008 in International Application No. PCT/EP2007/060449, filed Oct. 2, 2007.
"Ministerio de ambiente, vivienda y desarrollo territorial, resolucion numero 1318" Internet Article, Jul. 26, 2006, XP002430403, Colombia, URL: http://www.minambiente.gov.co/prensa/gacetas/2006/julio/res_1318_060706.pdf> [retrieved on Apr. 20, 2007].

*Primary Examiner* — Kyle Purdy
(74) *Attorney, Agent, or Firm* — Brinks Gilson & Lione

(57) ABSTRACT

The present invention relates to liquid pesticide compositions which contain at least one N-phenylsemicarbazone of the formula A (A)

wherein $R^1$ and $R^2$ are each independently hydrogen, halogen, CN, $C_1$-$C_4$ alkyl, $C_1$-$C_4$ alkoxy, $C_1$-$C_4$ haloalkyl or $C_1$-$C_4$ haloalkoxy and $R^3$ is $C_1$-$C_4$ alkoxy, $C_1$-$C_4$ haloalkyl or $C_1$-$C_4$ haloalkoxy. The invention also relates to a process for preparing the liquid pesticide compositions and to spray liquors of the invention, respectively, and to their use for plant and material protection.

21 Claims, No Drawings

LIQUID PESTICIDE COMPOSITION CONTAINING N-PHENYLSEMICARBAZONE PESTICIDE COMPOUNDS

This application is a National Stage application of International Application No. PCT/EP2007/060449 filed Oct. 2, 2007, which claims the benefit of U.S. Provisional Application No. 60/849,145, filed Oct. 3, 2006, the entire contents of which is hereby incorporated herein by reference. This application also claims the benefit under 35 U.S.C. §119 of European Patent Application No. 06123698.0, filed Nov. 8, 2006, the entire contents of which is hereby incorporated herein by reference.

The present invention relates to liquid pesticide compositions which contain at least one N-phenylsemicarbazone of the formula A as defined hereinafter. The invention also relates to a process for preparing the liquid pesticide compositions and to spray liquors of the invention, respectively, and to their use for plant and material protection.

For the purpose of application by the end user, pesticide compounds may be formulated in solid forms, such as wettable powders and granules, as well as in liquid forms, such as emulsifiable concentrates (ECs) or suspension concentrates (SCs). The latter ones can be diluted with water for use in the field and thus usually provide an easy-to-handle way of application. However, like most active ingredients that are used as pesticides, N-phenylsemicarbazones of the formula A are only sparingly or even insoluble in hydrophilic media such as water, monohydric $C_1$-$C_4$ alcohols or polyhydric $C_2$-$C_4$ alcohols: for example, they usually have a water-solubility of not more than 2 g/l, and often much less, at 25° C./1013 mbar. Nonetheless, application of insecticides in the form of dilute aqueous suspension concentrates, i.e. in the form of spray liquors, is favorable for ease of application.

Suspension concentrates (SC's) are formulations, wherein the active ingredient is present in the form of finely divided solid particles, which are suspended (dispersed) in a liquid dispersing medium such as water or polyhydric alcohols, wherein the active ingredient is insoluble or only sparingly soluble (generally less than 2000 ppm). Suspension concentrates usually contain utilizing surface-active compounds (surfactants), such as dispersants and wetting agents for stabilising the active ingredient particles in the dispersing medium. In SCs, the particles of the active ingredient usually have average particle diameters of more than 2 µm, mostly in the range of from more than >2 to 20 µm.

Despite the aforementioned advantages associated with the usage of SCs, there is a number of problems known to the skilled person which are sometimes encountered with SCs as a result of settling during prolonged storage or storage at elevated temperatures, the resistance of settled particles to re-suspension and the formation of crystalline material upon storage. As a consequence, the formulations may be difficult to handle and the bioefficacy may be inconsistent. Moreover, since the particle size of the active ingredient particles is relatively large in SCs, it may often result in a relatively low efficacy. On the other hand, reduction of particle size is believed to impart instability to a formulation due to the increased specific surface of the active ingredient.

Recently, aqueous polymer compositions have been described, which contain the pesticide compound in the form of polymer enrobed particles (see e.g. WO 2006/015791). However, the process for preparing such compositions is rather tedious.

WO2006/002984 describes liquid pesticide compositions, wherein at least one organic pesticide compound is dissolved in a mixture of a water-miscible solvent and at least one non-ionic block-copolymer. Among many others, the pesticide compound may be a N-phenylsemicarbazone compound of the formula A. The solvent used is capable of dissolving the active ingredient and may contain water, provided that the weight ratio of water to solvent does not exceed 1:2.

N-phenylsemicarbazone compounds of the formula A

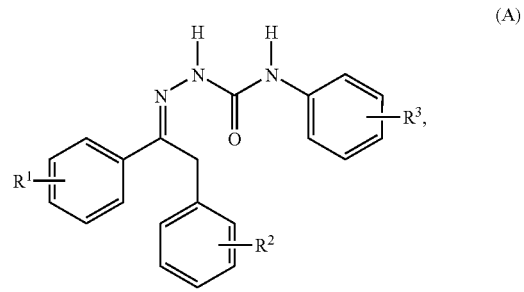

wherein $R^1$ and $R^2$ are each independently hydrogen, halogen, CN, $C_1$-$C_4$alkyl, $C_1$-$C_4$ alkoxy, $C_1$-$C_4$ haloalkyl or $C_1$-$C_4$ haloalkoxy and $R^3$ is $C_1$-$C_4$ alkoxy, $C_1$-$C_4$ haloalkyl or $C_1$-$C_4$ haloalkoxy, and their agriculturally acceptable salts are known from EP 0 462 456 A1. The compounds of the formula A have a wide pesticidal spectrum against arthropod pests and nematodes, in particular against insect pests.

The known formulations of N-phenylsemicarbazone insecticide compounds A have in common that they, in many cases, do not provide a satisfactory performance and/or suffer from the problems discussed above.

Therefore, it is an object of the present invention to provide a formulation for N-phenylsemicarbazone compounds A, which shows improved efficacy of the compound A and which has good stability properties. Upon dilution with water, the formulation should form a stable aqueous composition of the active ingredient. Moreover, the formulation should not form coarse material upon dilution with water and the active ingredient should be stable in the liquid concentrate formulation upon prolonged storage or storage at elevated temperatures. Moreover, the pesticide compositions should be producible in a simple manner.

Surprisingly this object could be achieved by the liquid pesticide composition wherein the compound A is present in the form of solid particles which are dispersed in the mixture of solvent and surfactant and which have a volume median diameter, as determined by dynamic light scattering, of not more than 1 µm.

Therefore, the present invention relates to a pesticide composition, which contains:

a) a pesticide N-phenylsemicarbazone compound of the general formula A, in particular a compound of the formula A, wherein $R^1$ is 3-$CF_3$ (meta position), $R^2$ is 4-CN (para position) and $R^3$ is 4-$OCF_3$ (para position), i.e. metaflumizone;

b) a solvent selected from water and polyhydric $C_2$-$C_4$ alcohols and mixtures thereof, the insecticide compound of the formula A being soluble in the solvent in an amount of not more than 2 g/l at 25° C./1013 mbar;

c) one or more surfactants;

wherein the compound A is present in the form of particles which are dispersed in the mixture of solvent and surfactant and which have a volume median diameter, as determined by dynamic light scattering, of less than 1 µm, frequently of not more than 0.9 µm, preferably not more than 800 nm, in particular not more than 700 nm, more preferably of not more than 500 nm, e.g. from 10 to <1000 nm, frequently from 20 to 900 nm, preferably from 50 to 800 nm, in particular from 70 to 700 nm and more preferably from 100 to 500 nm.

The average particle diameter as referred herein, are volume average particle diameters d(0.5) or d(v, 0.5), i.e. 50 vol.-% of the particles have a diameter which is above and 50 vol.-% of the particles have a diameter which is below the mean value cited. Therefore, average particle diameters are also termed "volume median diameters". Such average particle diameters can be determined by dynamic light scattering (usually performed on diluted suspensions containing from 0.01 to 1% by weight of the active ingredient A). A skilled person is familiar with these methods which are described e.g. in H. Wiese (D. Distler, Ed.), Aqueous Polymer Dispersions (Wassrige Polymerdispersionen), Wiley-VCH 1999, Chapter 4.2.1, p. 40ff, and the literature cited therein; H. Auweter, D. Horn, J. Colloid interf. Sci. 105 (1985), p. 399; D. Lilge, D. Horn, Colloid Polym. Sci. 269 (1991), p. 704; and H. Wiese, D. Horn, J. Chem. Phys. 94 (1991), p. 6429.

The liquid pesticide compositions of the present invention demonstrate an increased biological activity, namely by a factor of up to 2 times or more in comparison with similar concentrate compositions of the compound A containing a.i. particles having typical mean dimensions of significantly more than 1 µm and in particular more than 2 µm. Despite of the small particle size, the compositions of the present invention exhibit good stability over prolonged storage times, even at elevated temperatures, without significant occurrence of phase separation phenomena or noticeable agglomeration of the active ingredients. The compositions of the invention can be easily diluted with water to the desired application rate without the formation of coarse material or separation of the active ingredient. The dilutions remain stable for prolonged periods of time.

As used herein, the term $C_1$-$C_4$ alkyl, used as such as well as in related terms, such as $C_1$-$C_4$ alkoxy, $C_1$-$C_4$ haloalkyl or $C_1$-$C_4$ haloalkoxy, refers to straight or branched aliphatic alkyl groups having from 1 to 4 carbon atoms, e.g. methyl, ethyl, propyl, isopropyl, n-butyl, sec-butyl and tert-butyl.

As used herein, halogen, used as such as well as in related terms, such as haloalkyl or haloalkoxy, is selected from fluorine, chlorine, iodine and bromine, preferably from fluorine and chlorine, and more preferably is fluorine.

As used herein, the term $C_1$-$C_4$ alkoxy refers to a $C_1$-$C_4$ alkyl group, as defined above, which is linked via an oxygen atom, e.g. methoxy, ethoxy, propoxy, isopropoxy, n-butoxy, sec-butoxy and tert-butoxy.

As used herein, the term $C_1$-$C_4$ haloalkyl refers to a $C_1$-$C_4$alkyl group, as defined above, which additionally contains one or more, e.g. 2, 3, 4, 5 or 6, halogen atom(s), as defined above, e.g. mono- di- and trifluoromethyl, mono- di- and trichloromethyl, 1-fluoroethyl, 1-chloroethyl, 2-fluoroethyl, 2-chloroethyl, 1,1-difluoroethyl, 1,1-dichloroethyl, 1,2-difluoroethyl, 1,2-dichloroethyl, 2,2-difluoroethyl, 2,2-dichloroethyl, 2,2,2-trifluoroethyl and 2,2,2-trichloroethyl.

As used herein, the term $C_1$-$C_4$ haloalkoxy refers to a $C_1$-$C_4$alkoxy group, as defined above, which additionally contains one or more, e.g. 2, 3, 4, 5 or 6, halogen atom(s), as defined above, e.g. mono- di- and trifluoromethoxy, mono- di- and trichloromethoxy, 1-fluoroethoxy, 1-chloroethoxy, 2-fluoroethoxy, 2-chloroethoxy, 1,1-difluoroethoxy, 1,1-dichloroethoxy, 1,2-difluoroethoxy, 1,2-dichloroethoxy, 2,2-difluoroethoxy, 2,2-dichloroethoxy, 2,2,2-trifluoroethoxy and 2,2,2-trichloroethoxy.

As used herein, polyhydric $C_2$-$C_4$ alcohol refers to an alkanol which has from 2 to 4 carbon atoms and which carries two or more, e.g. 3 or 4, OH moieties, examples including ethylene glycol, 1,2-propane diol, 1,3-propane diol, 1,4 butane diol and glycerol.

Among the phenylsemicarbazones of formula A, preference is given to those in which the variables $R^1$, $R^2$ and $R^3$, independently of one another, but in particular in combination, have the meanings given below:
$R^1$ is $C_1$-$C_4$ haloalkyl, in particular trifluoromethyl;
$R^2$ is cyano;
$R^3$ is $C_1$-$C_4$ haloalkoxy, in particular trifluoromethoxy.

Most suitable is a compound of the formula A, wherein $R^1$ is 3-$CF_3$ (meta position), $R^2$ is 4-CN (para position) and $R^3$ is 4-$OCF_3$ (para position), i.e. metaflumizone. Metaflumizone is the common name of 2-[2-(4-cyanophenyl)-1-[3-(trifluoromethyl)-phenyl]ethylidene]-N-[4-(trifluoromethoxy)phenyl]hydrazinecarboxamide (IUPAC nomenclature: (E2)-2'-[2-(4-cyanophenyl)-1-(α,α,α-trifluoro-m-tolyl)ethylidene]-4-(trifluoromethoxy)carbanilohydrazide), having the following structure (Aa):

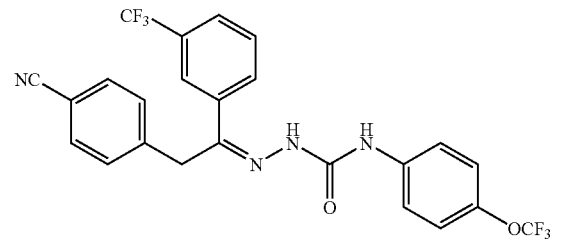

The compound exists in two geometric isomers with regard to the C—N double bond, i.e. 4-{(2E)-2-({[4-(trifluoromethoxy)anilino]carbonyl}hydrazono)-2-[3-(trifluoromethyl)-phenyl]ethyl}benzonitrile and 4-{(2Z)-2-({[4-(trifluoromethoxy)anilino]carbonyl}-hydrazono)-2-[3-(trifluoromethyl)phenyl]ethyl}benzonitrile. It is to be understood that the term "metaflumizone" includes both the E- and Z-isomer of the compound as defined above, as well as any mixture thereof in any ratio. E- and Z-isomers of compounds A and Aa and their interconversion have been described in general in WO05/047235, incorporated herein by reference. In particular, reference is made to the description of the above geometric isomers of metaflumizone, which WO05/047235 refers to as A-E and A-Z (or Aa-E and Aa-Z), their synthesis and conversion (examples 1 to 3 of WO05/047235) as well as mixtures of the E- and Z-isomer, especially with high E/Z-ratio. Because the pesticidal activity of the E-isomer is generally higher than that of the Z-isomer, metaflumizone having a E/Z-ratio higher than 1:1 may be preferred.

In the composition of the present invention the compound A is present in the form of solid a.i. particles, i.e. the particles do not contain polymer material but mainly the pure compound A. The purity of compound A is usually at least 90% by weight, preferably at least 95% by weight, i.e. the compound A makes up at least 90% by weight, in particular at least 95% by weight of the insoluble material present in the composition. The compound A may be present in the neutral form or as a salt, which obtained by treating the compound A with a suitable base. In particular, the salts of A contain such cations which are the counter ion of the base. The base and likewise the counterion is preferably chosen as do not reduce the pesticidal effects of the phenylsemicarbazones, examples including sodium or potassium ion. Preferably the compound A is present in the neutral form, as depicted in formulae A and Aa.

The amount of pesticide compound A may usually be from 5 to 60% by weight, in particular from 10 to 55% by weight, more preferably from 20 to 50% by weight, based on the total weight of the composition.

According to the invention, the solvent is selected in such a way that the compound of the formula A (or Aa) is insoluble or only sparingly soluble, i.e. at 25° C./1013 mbar the solubility of the pesticide compound in the solvent contained in the composition is less than 2 g/l, particularly less than 0.2 g/l, and more particularly less than 0.02 g/l. Solvents suitable for use in the present invention are selected from water and polyhydric $C_2$-$C_4$ alcohols and mixtures thereof.

The amount of solvent may usually be from 30 to 94.9% by weight, in particular from 40 to 89.5% by weight, more preferably from 45 to 79% by weight, based on the total weight of the composition.

If the solvent contains a polyhydric $C_2$-$C_4$ alcohol, it is preferably selected from the group consisting of ethylene glycol, 1,2-propane diol, 1,3-propane diol, glycerol and 1,4-butane diol; and more preferably from ethylene glycol and 1,3-propane diol.

In a first preferred embodiment of the invention the solvent consists mainly of water, i.e. water makes up at least 99% by weight of the total amount of solvent present in the composition. In a more preferred embodiment of the invention the solvent is a mixture of the aforementioned polyhydric $C_2$-$C_4$ alcohol and water. In the latter case, the weight ratio of water to polyhydric alcohol in the solvent preferably is in the range of from 99:1 to 1:1; more preferably in the range of from 50:1 to 2:1; and most preferably in the range of from 40:1 to 10:1. In another embodiment of the present invention the solvent b) comprises more than 50% by weight of a polyhydric $C_2$-$C_4$ alcohol, based on the total weight of the solvent.

According to the present invention, the pesticide composition comprises one or more surfactants. The surfactants may be ionic and/or non-ionic in nature. Surfactants may have a number average molecular weight $M_N$ of not more than 1000 Dalton or above 1000 Dalton, the latter ones (i.e. those having a $M_N$>1000 Dalton) hereinafter also being referred to as polymeric surfactants. While the nature of the surfactants c) is not particularly critical, e.g. they may be selected from any known dispersing agents and wetting agents. Dispersing agents are those surfactants which primarily bond to the surface of the active ingredient particles by ionic and/or hydrophobic interaction and which stabilize the particles in the liquid phase. Wetting agents are surfactants which primarily lower the interfacial tension between the liquid phase and the surface of the solid particles of the active ingredient (here, the pesticide compound of the formula A) that are dispersed in the liquid phase, thereby assisting in stabilizing the particles in the liquid phase. Wetting agents may be chosen by physical measuring of the contact angle. In particular a suitable wetting agent has a contact angle of less than 90°, in particular less than 60° (determined at 24° C./1013 mbar for a 1 M aqueous solution of the wetting agent according to DIN 53914 by the Wilhelmy method or according to extended Washburn method using a powder of compound A).

In general, liquid pesticide compositions of the present invention contain the at least one surfactant in amounts from 0.1 to 20% by weight, preferably from 0.5 to 15% by weight and in particular from 1 to 10% by weight, based on the total weight of the composition. Usually, the weight ratio of the insecticide compound A to the surfactant is in the range of from 2:1 to 50:1, and particularly from 3:1 to 20:1.

Thus, a preferred embodiment of the present invention relates to a pesticide composition, which contains:

a) 5 to 60% by weight, in particular from 10 to 55% by weight, more preferably from 20 to 50% by weight, based on the total weight of the composition, of a pesticide N-phenylsemicarbazone compound of the general formula A, in particular metaflumizone;

b) 30 to 94.9% by weight, in particular from 40 to 89.5% by weight, more preferably from 45 to 79% by weight, based on the total weight of the composition, of a solvent selected from water and polyhydric $C_2$-$C_4$ alcohols and mixtures thereof, the insecticide compound of the formula A being soluble in the solvent in an amount of not more than 2 g/l at 25° C./1013 mbar, particularly less than 0.2 g/l, and more particularly less than 0.02 g/l, with preference given to mixtures of water and polyhydric $C_2$-$C_4$ alcohols, wherein the weight ratio of water and polyhydric $C_2$-$C_4$ alcohol is in the range of from 99:1 to 1:1; more preferably in the range of from 50:1 to 2:1; and most preferably in the range of from 40:1 to 10:1;

c) from 0.1 to 20% by weight, preferably from 0.5 to 15% by weight and in particular from 1 to 10% by weight, based on the total weight of the composition, of one or more surfactants, the weight ratio of the insecticide compound A to the surfactant being preferably in the range of from 2:1 to 50:1, and particularly from 3:1 to 20:1;

wherein the compound A is present in the form of particles which are dispersed in the mixture of solvent and surfactant and which have a volume median diameter, as determined by dynamic light scattering, of less than 1 µm, frequently of not more than 0.9 µm, preferably not more than 800 nm, in particular not more 700 nm, more preferably of not more than 500 nm, e.g. from 10 to <1000 nm, frequently from 20 to 900 nm, preferably from 50 to 800 nm, in particular from 70 to 700 nm and more preferably from 100 to 500 nm.

Suitable surfactants are well known to the skilled person as are processes for the preparation thereof; they are also commercially available, e.g. under the trade names mentioned below in each case.

Preference is given to those compositions, wherein the surfactant comprises at least one anionic surfactant. In a very preferred embodiment of the present invention, the surfactant additionally comprises at least one non-ionic surfactant. If the composition contains a combination of at least one anionic surfactant and at least one non-ionic surfactant, the weight ratio of anionic surfactant and non-ionic surfactant is preferably from 1:5 to 5:1, in particular from 1:3 to 3:1. However, the non-ionic surfactant may also be the only surfactant present in the composition of the present invention.

Thus, a preferred embodiment of the present invention relates to a pesticide composition, which contains:

a) 5 to 60% by weight, in particular from 10 to 55% by weight, more preferably from 20 to 50% by weight, based on the total weight of the composition, of a pesticide N-phenylsemicarbazone compound of the general formula A, in particular metaflumizone;

b) 30 to 94.9% by weight, in particular from 40 to 89.5% by weight, more preferably from 45 to 79% by weight, based on the total weight of the composition, of a solvent selected from water and polyhydric $C_2$-$C_4$ alcohols and mixtures thereof, the insecticide compound of the formula A being soluble in the solvent in an amount of not more than 2 g/l at 25° C./1013 mbar, particularly less than 0.2 g/l, and more particularly less than 0.02 g/l, with preference given to mixtures of water and polyhydric $C_2$-$C_4$ alcohols, wherein the weight ratio of water and polyhydric $C_2$-$C_4$ alcohol is in the range of from 99:1 to 1:1; more preferably in the range of from 50:1 to 2:1; and most preferably in the range of from 40:1 to 10:1;

c) from 0.1 to 20% by weight, preferably from 0.5 to 15% by weight and in particular from 1 to 10% by weight, based on the total weight of the composition, of a combination of at least one anionic surfactant and at least one non-ionic surfactant, the weight ratio of anionic surfactant and non-ionic surfactant being preferably from 1:5 to 5:1, in particular from 1:3 to 3:1, and the weight ratio of the insecticide compound A to the surfactant being preferably in the range of from 2:1 to 50:1, and particularly from 3:1 to 20:1;

wherein the compound A is present in the form of particles which are dispersed in the mixture of solvent and surfactant and which have a volume median diameter, as determined by dynamic light scattering, of less than 1 μm, frequently of not more than 0.9 μm, preferably not more than 800 nm, in particular not more 700 nm, more preferably of not more than 500 nm, e.g. from 10 to <1000 nm, frequently from 20 to 900 nm, preferably from 50 to 800 nm, in particular from 70 to 700 nm and more preferably from 100 to 500 nm.

Thus, another preferred embodiment of the present invention relates to a pesticide composition, which contains:

a) 5 to 60% by weight, in particular from 10 to 55% by weight, more preferably from 20 to 50% by weight, based on the total weight of the composition, of a pesticide N-phenylsemicarbazone compound of the general formula A, in particular metaflumizone;

b) 30 to 94.9% by weight, in particular from 40 to 89.5% by weight, more preferably from 45 to 79% by weight, based on the total weight of the composition, of a solvent selected from water and polyhydric $C_2$-$C_4$ alcohols and mixtures thereof, the insecticide compound of the formula A being soluble in the solvent in an amount of not more than 2 g/l at 25° C./1013 mbar, particularly less than 0.2 g/l, and more particularly less than 0.02 g/l, with preference given to mixtures of water and polyhydric $C_2$-$C_4$ alcohols, wherein the weight ratio of water and polyhydric $C_2$-$C_4$ alcohol is in the range of from 99:1 to 1:1; more preferably in the range of from 50:1 to 2:1; and most preferably in the range of from 40:1 to 10:1;

c) from 0.1 to 20% by weight, preferably from 0.5 to 15% by weight and in particular from 1 to 10% by weight, based on the total weight of the composition, of one or more surfactants, which are selected from non-ionic surfactants, the weight ratio of the insecticide compound A to the surfactant being preferably in the range of from 2:1 to 50:1, and particularly from 3:1 to 20:1;

wherein the compound A is present in the form of particles which are dispersed in the mixture of solvent and surfactant and which have a volume median diameter, as determined by dynamic light scattering, of less than 1 μm, frequently of not more than 0.9 μm, preferably not more than 800 nm, in particular not more 700 nm, more preferably of not more than 500 nm, e.g. from 10 to <1000 nm, frequently from 20 to 900 nm, preferably from 50 to 800 nm, in particular from 70 to 700 nm and more preferably from 100 to 500 nm.

In one embodiment of the present invention, the pesticide compositions contain at least one non-polymeric surfactant c) having a number average molecular weight $M_N$ of not more than 1000 Dalton. In a preferred embodiment, the pesticide compositions of the present invention contain at least one polymeric surfactant having a $M_N$ of at least 1200 Dalton, e.g. ranging from 1200 to 100000 Dalton, preferably ranging from 1500 to 60000 Dalton, and most preferably ranging from 2000 to 20000 Dalton. In a very preferred embodiment the surfactant comprises a combination of at least one polymeric surfactant and at least one non-polymeric surfactant. If the composition contains a combination of at least one polymeric surfactant and at least one non-polymeric surfactant, the weight ratio of polymeric surfactant and non-polymeric surfactant is preferably from 1:5 to 5:1, in particular from 1:3 to 3:1.

In a very preferred embodiment of the invention, the pesticide compositions contain at least one non-ionic polymeric surfactant having a number average molecular weight $M_N$ of at least 1200 Dalton, e.g. ranging from 1200 to 100000 Dalton, preferably ranging from 1500 to 60000 Dalton, and most preferably ranging from 2000 to 20000 Dalton. In this embodiment, the composition may additionally contain one or more anionic surfactants which may be polymeric or non-polymeric or at least one further non-ionic, non-polymeric surfactant.

In another very preferred embodiment of the invention, the pesticide compositions contain at least one anionic polymeric surfactant having a number average molecular weight $M_N$ of at least 1200 Dalton, e.g. ranging from 1200 to 100000 Dalton, preferably ranging from 1500 to 60000 Dalton, and most preferably ranging from 2000 to 20000 Dalton. In this embodiment, the composition may additionally contain one or more non-ionic surfactants which may be polymeric or non-polymeric.

Thus, a very preferred embodiment of the present invention relates to a pesticide composition, which contains:

a) 5 to 60% by weight, in particular from 10 to 55% by weight, more preferably from 20 to 50% by weight, based on the total weight of the composition, of a pesticide N-phenylsemicarbazone compound of the general formula A, in particular metaflumizone;

b) 30 to 94.9% by weight, in particular from 40 to 89.5% by weight, more preferably from 45 to 79% by weight, based on the total weight of the composition, of a solvent selected from water and polyhydric $C_2$-$C_4$ alcohols and mixtures thereof, the insecticide compound of the formula A being soluble in the solvent in an amount of not more than 2 g/l at 25° C./1013 mbar, particularly less than 0.2 g/l, and more particularly less than 0.02 g/l, with preference given to mixtures of water and polyhydric $C_2$-$C_4$ alcohols, wherein the weight ratio of water and polyhydric $C_2$-$C_4$ alcohol is in the range of from 99:1 to 1:1; more preferably in the range of from 50:1 to 2:1; and most preferably in the range of from 40:1 to 10:1;

c) from 0.1 to 20% by weight, preferably from 0.5 to 15% by weight and in particular from 1 to 10% by weight, based on the total weight of the composition, of a combination of at least one polymeric surfactant as defined above, in particular a non-ionic polymeric surfactant, and at least one non-polymeric surfactant, in particular a non-ionic non-polymeric surfactant and/or an anionic non-polymeric surfactant, the weight ratio of polymeric surfactant and non-polymeric surfactant being preferably from 1:5 to 5:1, in particular from 1:3 to 3:1, and the weight ratio of the insecticide compound A to the surfactant being preferably in the range of from 2:1 to 50:1, and particularly from 3:1 to 20:1;

wherein the compound A is present in the form of particles which are dispersed in the mixture of solvent and surfactant and which have a volume median diameter, as determined by dynamic light scattering, of less than 1 µm, frequently of not more than 0.9 µm, preferably not more than 800 nm, in particular not more 700 nm, more preferably of not more than 500 nm, e.g. from 10 to <1000 nm, frequently from 20 to 900 nm, preferably from 50 to 800 nm, in particular from 70 to 700 nm and more preferably from 100 to 500 nm.

Anionic surfactants include in particular the sodium, potassium calcium or ammonium salts of non-polymeric anionic surfactants having an $SO_3^-$ or $PO_3^{2-}$ group, e.g.
- c.1 $C_6$-$C_{22}$-alkylsulfonates such as lauryl sulfonate, isotridecylsulfonate;
- c.2 $C_6$-$C_{22}$-alkylsulfates such as lauryl sulfate, isotridecylsulfate, cetylsulfate, stearylsulfate;
- c.3 aryl- and $C_1$-$C_{16}$-alkylarylsulfonates such as naphthylsulfonate, mono-, di- and tri-$C_1$-$C_{16}$-alkylnaphthylsulfonates such as dibutylnaphtylsulfonate, dodecyidiphenylether sulfonate, mono-, di- and tri-$C_1$-$C_{16}$-alkylphenylsulfonates such as cumylsulfonate, octylbenzene sulfoanate, nonylbenzenesulfonate, dodecylbenzene sulfonate and tridecylbenzene sulfonate;
- c.4 sulfates and sulfonates of $C_6$-$C_{22}$-fatty acids and $C_6$-$C_{22}$-fatty acid esters;
- c.5 sulfates of ethoxylated $C_6$-$C_{22}$ alkanoles such as sulfates of (poly)ethoxylated lauryl alcohol;
- c.6 sulfates of (poly)ethoxylated $C_4$-$C_{16}$-alkylphenols;
- c.7 mono- and diesters of phosphorous acid, including mixtures thereof with triesters and salts thereof, in particular the esters with $C_8$-$C_{22}$-alkanols, ethoxylated $C_8$-$C_{22}$-alkanols, $C_4$-$C_{22}$-alkylphenols, (poly)ethoxylated $C_4$-$C_{22}$-alkylphenols, di- or tristyrylphenols, (poly)ethoxylated di- or tristyrylphenols; and
- c.8 di $C_4$-$C_{16}$ alkylesters of sulfosuccinic acid such as dioctylsulfosuccinate.

polymeric anionic surfactants having an $SO_3^-$ or $PO_3^{2-}$ group, e.g.
- c.9 condensates of arylsulfonic acid with formaldehyde and optionally with urea.

non-polymeric anionic surfactants having at least one carboxylate group, e.g.
- c.10 fatty acids such as stearates and
- c.11 N—$C_6$-$C_{22}$-acylglutamates.

polymeric anionic surfactants having carboxylate groups, e.g.
- c.12 anionic graft copolymers containing polyethylene oxide moiety PEO grafted on a polymeric backbone and carboxylate groups attached to the polymer backbone.
- c.13 anionic copolymers containing, in polymerised form, (i) $C_3$-$C_5$ monoethylenically unsaturated carboxylic acid monomers, and optionally (ii) hydrophobic monomers having a water solubility of not more than 60 g/l at 20° C. and 1013 mbar.

Amongst anionic surfactants those of the groups c.1, c.3, c.8, c.9, c.12 and c.13 and mixtures thereof are preferred.

In the group of surfactants c.3 preference is given to mono- or di-$C_4$-$C_8$-alkylnaphthaline sulfonic acid and mono- or di-$C_4$-$C_{16}$-alkylbenzesulfonic acid and the alkaline metal salts, such as the sodium or potassium salt, and the earth alkaline metal salts, in particular the calcium salts thereof. A particularly suitable example is Morwet® EFW (Akzo Nobel), and the like.

In the group of surfactants c.8 preference is given to the alkaline metal salts of di($C_6$-$C_{12}$ alkyl) sulfosuccinates, $C_6$-$C_{12}$ alkyl being a straight chain or branched alkyl group of from 6 to 12 carbon atoms, e.g. n-hexyl, n-heptyl, n-octyl, n-nonyl, n-decyl, n-dodecyl, 2-hexyl, 2-heptyl, 2-octyl, 2-nonyl and 2-ethyl hexyl. Preferably, an alkaline metal dioctyl sulfosuccinate is employed, wherein the octyl moiety may be linear or branched and wherein the alkaline metal being selected from sodium and potassium. A particularly suitable example is Aerosol® OTB (Cytec), and the like.

In the group of surfactants c.9 the aryl sulfonic acid may be e.g. phenol sulfonic acid and naphthalene sulfonic acid which are unsubstituted or substituted by one or more, e.g. 1, 2, 3 or 4, $C_1$-$C_{20}$ alkyl groups. In a preferred embodiment, the surfactants c.9 is an alkaline metal salts or earth alkaline metal salt of a reaction product (condensate) of naphthalene sulfonic acid and formaldehyde; a particularly suitable example is Morwet® D425 (Akzo Nobel).

Preferred graft copolymers of the group c.12 contain, in polymerised form, (i) $C_3$-$C_5$ monoethylenically unsaturated carboxylic acid monomers, such as acrylic acid, methacrylic acid and maleic acid, (ii) polyethylenoxide groups which are attached either via ester linkages or ether linkages to the polymer backbone and optionally (iii) hydrophobic monomers having a water solubility of not more than 60 g/l at 20° C. and 1013 mbar, e.g. $C_1$-$C_6$-alkylesters of $C_3$-$C_5$ monoethylenically unsaturated carboxylic acid monomers such as $C_1$-$C_6$ alkylacrylates and -methacrylates, vinylaromatic monomers such as styrene and $C_2$-$C_{12}$-monolefines such as ethene, propene, 1-butene, isobutene, hexene, 2-ethylhexene, diisobutene (mixture of isobuten dimers), tripropene, tetrapropene, triisobutene etc. In a preferred embodiment, the anionic backbone of the surfactants c.12 contains, in polymerized form, methacrylic acid, methyl methacrylate and polyethylene oxide esters of methacrylic acid.

Preferred polymeric surfactants of the group c.13 are those which contain, in polymerized form (i) at least one $C_3$-$C_5$ monoethylenically unsaturated carboxylic acid monomer, and (ii) at least one hydrophobic monomers as defined above. Suitable $C_3$-$C_5$ monoethylenically unsaturated carboxylic acid monomer and suitable hydrophobic monomers are those mentioned in the group c.13. Preferred $C_3$-$C_5$ monoethylenically unsaturated carboxylic acid monomers include acrylic acid, methacrylic acid and maleic acid. Preferred hydrophobic monomers are selected from vinylaromatic monomers such as styrene monomers and $C_2$-$C_{12}$-monolefines. Preferably, the polymeric surfactants c.13 contain, in polymerised form, (i) at least one $C_3$-$C_5$ monoethylenically unsaturated carboxylic acid monomer, in particular acrylic acid or methacrylic acid, and (ii) at least one hydrophobic monomer selected from styrene monomers and $C_2$-$C_{12}$-monolefines. The weight ratio from acid monomer to hydrophobic monomer is preferably in the range of from 10:1 to 1:3; preferably from 5:1 to 1:2. A particularly suitable example for surfactans c.13 is Atlox® Metasperse 500 L (Uniqema), and the like.

Non-ionic surfactants include in particular
- c.14 polyethyleneglycol-$C_1$-$C_{22}$-alkylethers, polyethyleneglycol/polypropyleneglycol-$C_1$-$C_{22}$-alkylethers, in particular polyethoxylates and poly-ethoxylates-co-propoxylates of linear or branched $C_8$-$C_{20}$-alkanoles, more preferably polyethoxylated $C_8$-$C_{22}$-fatty alcohols and polyethoxylated $C_8$-$C_{22}$-oxoalcohols, such as polyethoxylated lauryl alcohol, polyethoxylated isotridecanol, polyethoxylated cetyl alcohol, polyethoxylated stearyl alcohol, poly-ethoxylates-co-propoxylates of laurylalcohol, poly-ethoxylates-co-propoxylates of cetylalcohol, poly-ethoxylates-co-propoxylates of isotridecylalcohol, poly-ethoxylates-co-propoxylates of stearylalcohol, and esters thereof, such as acetates;

c.15 polyethylenglycol arylethers and polyethyleneglycol/polypropyleneglycol arylethers, in particular polyethoxylates and poly-ethoxylates-co-propoxylates of mono- or di-$C_1$-$C_{16}$-alkylphenoles, such as polyethoxylates and poly-ethoxylates-co-propoxylates of nonylphenol, decylphenol, isodecylphenol, dodecylphenol or isotridecylphenol, polyethoxylates and polyethoxylates-co-propoxylates of mono-, di- und tristyrylphenoles; and the esters thereof, e.g. the acetates;

c.16 $C_6$-$C_{12}$-alkylglucosides and $C_6$-$C_{22}$-alkyl polyglucosides;

c.17 partial esters of polyols with $C_6$-$C_{22}$-alkanoic acids, in particular mono- and diesters of glycerine and mono-, di- and triesters of sorbitan, such as glycerine monostearate, sorbitanmonooleat, sorbitantristearat;

c.18 polyethoxylates of $C_6$-$C_{22}$-alkylglucosides and polyethoxylates of $C_6$-$C_{22}$-alkyl polyglucosides;

c.19 polyethoxylates and poly-ethoxylates-co-propoxylates of $C_6$-$C_{22}$-fatty amines;

c.20 polyethoxylates and poly-ethoxylates-co-propoxylates of $C_6$-$C_{22}$-fatty acids and polyethoxylates and poly-ethoxylates-co-propoxylates of hydroxyl $C_6$-$C_{22}$-fatty acids;

c.21 polyethoxylates of partial esters of polyols with $C_6$-$C_{22}$-alkanoic acids, in particular polyethoxylates of mono- and diesters of glycerine and polyethoxylates of mono-, di- and triesters of sorbitan, such as polyethoxylates of glycerine monostearate, polyethoxylates of sorbitanmonooleat, polyethoxylates of sorbitanmonostearat and polyethoxylates of sorbitantristearat;

c.22 polyethoxylates of vegetable oils or animal fats such as corn oil ethoxylate, castor oil ethoxylate, tallow oil ethoxylate;

c.23 polyethoxylates of fatty amines, fatty amides or of fatty acid diethanolamides.

c.24 polyethoxylates and poly-ethoxylates-co-propoxylates of mono-, di- und tristyrylphenoles; and the esters thereof, e.g. the acetates; and c.25 non-ionic block copolymers comprising at least one poly(ethylene oxide) moiety PEO and at least one polyether moiety PAO derived from $C_3$-$C_{10}$-alkylene oxides and/or styrene oxide, in particular polyoxyethylene-polyoxypropylene-blockcopolymers.

c.26 non-ionic graft copolymers containing polyethylene oxide moiety PEO grafted on a non-ionic, hydrophilic polymeric backbone.

The terms polyethyleneglycol, polyethoxylates and poly-ethoxylated refer to polyether radicals derived from ethyleneoxide. Likewise, the term poly-ethoxylate-co-propoxylate refers to a polyether radical derived from a mixture of ethyleneoxide and propylenoxide. Thus polyethoxylates have repeating units of the formula [$CH_2CH_2O$] while poly-ethoxylate-co-propoxylate have repeating units of the formulae [$CH_2CH_2O$] and [$CH(CH_3)CH_2O$]. The surfactants c.14, c.15 and c.18 to c.24 may belong to the group of non-polymeric surfactants or to the group of polymeric surfactants, depending on the number of alkylene oxide repeating units. In the surfactants of these groups, the number of such repeating units will generally range from 2 to 200, in particular from 3 to 100, especially from 3 to 50. The surfactants of the groups c.17 and c.18 belong to non-polymeric surfactants while the surfactants of groups c.25 and c.26 are usually polymeric surfactants.

Amongst non-ionic surfactants those of the groups c.14, c.15, c.24, c.25 and c.26 and mixtures thereof are preferred.

In the group of surfactants c.14 preference is given to polyethoxylates and poly(ethoxylate-co-propoxylates) of linear $C_8$-$C_{22}$ alkanols. Likeweise preferred are poly (ethoxylate-co-propoxylates) of $C_1$-$C_{10}$ alkanols, with particular preference given to butanol. Amongst the surfactants c.14 those are preferred which have a number average molecular weight $M_N$ of not more than 5000 Dalton. Particular preference is given to poly(ethoxylate-co-propoxylates) of $C_1$-$C_{10}$ alkanols, having a number average molecular weight $M_N$ of from 500 to 5000 Dalton Particularly suitable examples include Atlox® G 5000 (Akzo Nobel), Tergitol®XD and the like.

In the surfactants of the group c.24 a phenoxy radical carries 1, 2 or 3 styryl moieties and a polyethylene oxide moiety PEO or a poly(ethylenoxide-co-propylenoxide) moiety PEO/PPO. The PEO moiety typically comprises from 5 to 50 ethylene oxide groups. Preferred surfactants c.24 may be represented by the formula $(C_2H_4O)_n.C_{30}H_{30}O$, wherein n is an integer of from 5 to 50 and $C_{30}H_{30}O$ represents a tri(styryl) phenol group. A particularly suitable example is Soprophor® BSU (Rhodia).

The non-ionic block copolymers of the surfactant class c.25 comprise at least one poly(ethylene oxide) moiety PEO and at least one hydrophobic polyether moiety PAO. The PAO moiety usually comprises at least 3, preferably at least 5, in particular 10 to 100 repeating units (number average) which are derived from $C_3$-$C_{10}$ alkylene oxides, such as propylene oxide, 1,2-butylene oxide, cis- or trans-2,3-butylene oxide or isobutylene oxide, 1,2-pentene oxide, 1,2-hexene oxide, 1,2-decene oxide and styrene oxide, among which $C_3$-$C_4$alkylene oxides are preferred. Preferably, the PAO moieties comprise at least 50% by weight, and more preferably at least 80% by weight of repeating units derived from propylene oxide. The PEO moieties usually comprise at least 3, preferably at least 5, and more preferably at least 10 repeating units derived from ethylene oxide (number average). The weight ratio of PEO moieties and PAO moieties (PEO:PAO) usually ranges from 1:10 to 10:1, preferably from 1:10 to 2:1, more preferably from 2:8 to 7:3 and in particular from 3:7 to 6:4. Those surfactants c3) are preferred which have a number average molecular weight $M_N$ ranging from more than 1200 to 100000 Dalton, preferably from 2000 to 60000 Dalton, more preferably from 2500 to 50000 Dalton and in particular from 3000 to 20000 Dalton. In general, the PEO moieties and the PAO moieties make up at least 80% by weight, and preferably at least 90% by weight, e.g. 90 to 99.5% by weight, of the non-ionic block copolymer surfactants c3). Suitable surfactants c3) are described e.g. in WO2006/002984, in particular those having the formulae P1 to P5 given therein.

The non-ionic block copolymer surfactants of the group c.25 described herein are commercially available e.g. under the trade names Pluronic®, such as Pluronic® P 65, P84, P 103, P 105, P 123 and Pluronic® L 31, L 43, L 62, L 62 LF, L 64, L 81, L 92 and L 121, Pluraflo® such as Pluraflo® L 860, L1030 and L 1060; Tetronic®, such as Tetronic® 704, 709, 1104, 1304, 702, 1102, 1302, 701, 901, 1101, 1301 (BASF Aktiengesellschaft), Agrilan® AEC 167 and Agrilan® AEC 178 (Akcros Chemicals), Antarox® B/848 (Rhodia), Berol® 370 and Berol® 374 (Akzo Nobel Surface Chemistry), Dowfax® 50 C15, 63 N10, 63 N30, 64 N40 and 81 N10 (Dow Europe), Genapol® PF (Clariant), Monolan®, such as Monolan® PB, Monolan® PC, Monolan® PK (Akcros Chemicals), Panox® PE (Pan Asian Chemical Corporation), Symperonic®, such as Symperonic® PE/L, Symperonic® PE/F, Symperonic® PE/P, Symperonic® PE/T (ICI Surfactants), Tergitol® XD, Tergitol® XH and Tergitol® XJ (Union Carbide), Triton® CF-32 (Union Carbide), Teric PE Series (Huntsman) and Witconol®, such as Witconol® APEB, Witconol® NS 500 K and the like. Among these, the Pluronic® and the Pluraflo® block copolymers are preferred, particularly suitable examples being Pluronic®) P105 and Pluraflo® 1060, and the like.

Preferred graft copolymers of the group c.26 contain, in polymerised form, (i) methyl esters or hydroxyl-$C_2$-$C_3$-alkyl esters of $C_3$-$C_5$ monoethylenically unsaturated carboxylic acid monomers, such as methyl acrylate, methyl methacrylate, hydroxyethyl acrylate and hydroxyethyl methacrylate and (ii) polyethylenoxide groups which are attached either via ester linkages or ether linkages to the polymer backbone. In a preferred embodiment, the backbone of the surfactants c.26 contains, in polymerized form, methyl methacrylate and polyethylene oxide esters of methacrylic acid, a particularly suitable example being Atlox® 4913 (Akzo Nobel), and the like.

In a very preferred embodiment of the present invention, the liquid pesticide compositions comprise at least one polymeric surfactant of the groups c.24, c.25 and c.26 and at least one further surfactant, selected from non-polymeric non-ionic surfactants, anionic non-polymeric surfactants and anionic polymeric surfactants. Preferably the further surfactant is selected from the groups c.8, c.9, c.14 and c.15.

Thus, a very preferred embodiment of the present invention relates to a pesticide composition, which contains:
a) 5 to 60% by weight, in particular from 10 to 55% by weight, more preferably from 20 to 50% by weight, based on the total weight of the composition, of a pesticide N-phenylsemicarbazone compound of the general formula A, in particular metaflumizone;
b) 30 to 94.9% by weight, in particular from 40 to 89.5% by weight, more preferably from 45 to 79% by weight, based on the total weight of the composition, of a solvent selected from water and polyhydric $C_2$-$C_4$ alcohols and mixtures thereof, the insecticide compound of the formula A being soluble in the solvent in an amount of not more than 2 g/l at 25° C./1013 mbar, particularly less than 0.2 g/l, and more particularly less than 0.02 g/l, with preference given to mixtures of water and polyhydric $C_2$-$C_4$ alcohols, wherein the weight ratio of water and polyhydric $C_2$-$C_4$ alcohol is in the range of from 99:1 to 1:1; more preferably in the range of from 50:1 to 2:1; and most preferably in the range of from 40:1 to 10:1;
c) from 0.1 to 20% by weight, preferably from 0.5 to 15% by weight and in particular from 1 to 10% by weight, based on the total weight of the composition, of a combination of at least one non-ionic polymeric surfactant of the groups c.24, c.25 and c.26, and at least one further surfactant, in particular a non-ionic non-polymeric surfactant and/or an anionic surfactant, which is preferably selected from the surfactants of the groups c.8, c.9, c.14 and c.15, the weight ratio of polymeric surfactant and further surfactant being preferably from 1:5 to 5:1, in particular from 1:3 to 3:1, and the weight ratio of the insecticide compound A to the surfactant being preferably in the range of from 2:1 to 50:1, and particularly from 3:1 to 20:1;

wherein the compound A is present in the form of particles which are dispersed in the mixture of solvent and surfactant and which have a volume median diameter, as determined by dynamic light scattering, of less than 1 μm, frequently of not more than 0.9 μm, preferably not more than 800 nm, in particular not more 700 nm, more preferably of not more than 500 nm, e.g. from 10 to <1000 nm, frequently from 20 to 900 nm, preferably from 50 to 800 nm, in particular from 70 to 700 nm and more preferably from 100 to 500 nm.

In a another preferred embodiment of the present invention, the compositions comprise at least one anionic polymeric surfactant selected from the class of surfactants c.9 as described above, and optionally one or two further surfactants, selected from non-polymeric non-ionic surfactants, polymeric non-ionic surfactants, and anionic non-polymeric surfactants. If present, the further surfactant is preferably selected from surfactants of the groups c.8, c.14, c.15, c.24, c.25 and c.26.

Thus, a very preferred embodiment of the present invention relates to a pesticide composition, which contains:
a) 5 to 60% by weight, in particular from 10 to 55% by weight, more preferably from 20 to 50% by weight, based on the total weight of the composition, of a pesticide N-phenylsemicarbazone compound of the general formula A, in particular metaflumizone;
b) 30 to 94.9% by weight, in particular from 40 to 89.5% by weight, more preferably from 45 to 79% by weight, based on the total weight of the composition, of a solvent selected from water and polyhydric $C_2$-$C_4$ alcohols and mixtures thereof, the insecticide compound of the formula A being soluble in the solvent in an amount of not more than 2 g/l at 25° C./1013 mbar, particularly less than 0.2 g/l, and more particularly less than 0.02 g/l, with preference given to mixtures of water and polyhydric $C_2$-$C_4$ alcohols, wherein the weight ratio of water and polyhydric $C_2$-$C_4$ alcohol is in the range of from 99:1 to 1:1; more preferably in the range of from 50:1 to 2:1; and most preferably in the range of from 40:1 to 10:1;
c) from 0.1 to 20% by weight, preferably from 0.5 to 15% by weight and in particular from 1 to 10% by weigh, based on the total weight of the composition, of a combination of at least one anionic polymeric surfactant of the group c.9, and one or two further surfactants, selected from non-polymeric non-ionic surfactants, polymeric non-ionic surfactants, and anionic non-polymeric surfactants, which are preferably selected from surfactants of the groups c.8, c.14, c.15, c.24, c.25 and c.26, the weight ratio of anionic surfactant and further surfactant being preferably from 1:10 to 10:1, in particular from 1:3 to 3:1, and the weight ratio of the insecticide compound A to the surfactant being preferably in the range of from 2:1 to 50:1, and particularly from 3:1 to 20:1;

wherein the compound A is present in the form of particles which are dispersed in the mixture of solvent and surfactant and which have a volume median diameter, as determined by dynamic light scattering, of less than 1 μm, frequently of not more than 0.9 μm, preferably not more than 800 nm, in particular not more 700 nm, more preferably of not more than 500 nm, e.g. from 10 to <1000 nm, frequently from 20 to 900 nm, preferably from 50 to 800 nm, in particular from 70 to 700 nm and more preferably from 100 to 500 nm.

In a particular preferred embodiment, the composition of the invention contain one or more non-ionic polymeric surfactants which are selected from the group c.25, one ore more anionic surfactant which are selected from the groups c.8 and c.9 and optionally a further non-ionic surfactant, which is selected from the groups c.14, c.15 and c.24.

Thus, a very preferred embodiment of the present invention relates to a pesticide composition, which contains:
a) 5 to 60% by weight, in particular from 10 to 55% by weight, more preferably from 20 to 50% by weight, based on the total weight of the composition, of a pesticide N-phenylsemicarbazone compound of the general formula A, in particular metaflumizone;

b) 30 to 94.9% by weight, in particular from 40 to 89.5% by weight, more preferably from 45 to 79% by weight, based on the total weight of the composition, of a solvent selected from water and polyhydric $C_2$-$C_4$ alcohols and mixtures thereof, the insecticide compound of the formula A being soluble in the solvent in an amount of not more than 2 g/l at 25° C./1013 mbar, particularly less than 0.2 g/l, and more particularly less than 0.02 g/l, with preference given to mixtures of water and polyhydric $C_2$-$C_4$ alcohols, wherein the weight ratio of water and polyhydric $C_2$-$C_4$ alcohol is in the range of from 99:1 to 1:1; more preferably in the range of from 50:1 to 2:1; and most preferably in the range of from 40:1 to 10:1;

c) from 0.1 to 20% by weight, preferably from 0.5 to 15% by weight and in particular from 1 to 10% by weight, based on the total weight of the composition, of a combination of one or more non-ionic polymeric surfactants which are selected from the group c.25, one ore more anionic surfactant which are selected from the groups c.8 and c.9 and optionally one or more further non-ionic non-polymeric surfactants, which are selected from the groups c.14, c.15 and c.24, and the weight ratio of the insecticide compound A to the surfactant being preferably in the range of from 2:1 to 50:1, and particularly from 3:1 to 20:1;

wherein the compound A is present in the form of particles which are dispersed in the mixture of solvent and surfactant and which have a volume median diameter, as determined by dynamic light scattering, of less than 1 μm, frequently of not more than 0.9 μm, preferably not more than 800 nm, in particular not more 700 nm, more preferably of not more than 500 nm, e.g. from 10 to <1000 nm, frequently from 20 to 900 nm, preferably from 50 to 800 nm, in particular from 70 to 700 nm and more preferably from 100 to 500 nm.

The components a), b) and c) (i.e. compound A, solvent and surfactant) will generally make up at least 90% by weight, preferably at least 95% by weight of the total weight of the composition. Usually the composition does not contain polymeric material, except for polymeric surfactants and polymeric viscosity-modifying agents.

The compositions according to the invention may also comprise customary additives, for example viscosity-modifying additives (thickeners), antifoams, bactericides and antifreeze agents. Such additives may be incorporated into the compositions of the invention either before or after step (i) of the preparation process described herein has been carried out. Preferably, these additives are added after step (ii) of the preparation process described herein has been carried out. The amount of additives will generally not exceed 10% by weight, in particular 5% by weight of the total weight of the composition.

Suitable thickeners are compounds which confer a pseudoplastic flow behavior to the formulation, i.e. high viscosity at rest and low viscosity in the agitated stage. Mention may be made, in this connection, for example, of commercial thickeners based on polysaccharides, such as Xanthan Gum® (Kelzan® from Kelco; Rhodopol® 23 from Rhone Poulenc or Veegum® from R. T. Vanderbilt), or phyllosilicates which may be hydrophobized, such as Attaclay® (from Engelhardt). Xanthan Gum® is a preferred thickener.

Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof.

Bactericides can be added to stabilize the compositions according to the invention against attack by microorganisms. Suitable bactericides are, for example, based on isothiazolones such as the compounds marketed under the trademarks Proxel® from Avecia (or Arch) or Acticide® RS from Thor Chemie and Kathon® MK from Rohm & Haas.

The compositions of the invention may optionally comprise also pigments or dyes, in particular, if the composition is intended for seed treatment purposes. Suitable pigments or dyes for seed treatment formulations are pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

In addition, the aqueous active compound compositions according to the invention can be formulated with conventional binders, for example aqueous polymer dispersions, water-soluble resins, for example water-soluble alkyd resins, or waxes.

The compositions of the present invention can be prepared by a process comprising the following steps:

(i) providing a suspension of the compound A in a mixture of the solvent and the surfactant;

(ii) reducing the particle size of compound A present in the suspension of step (i) to a volume median diameter of less than 1 μm, frequently to a volume median diameter of not more than 0.9 μm, preferably not more than 800 nm, in particular not more 700 nm, more preferably of not more than 500 nm, e.g. from 10 to <1000 nm, frequently from 20 to 900 nm, preferably from 50 to 800 nm, in particular from 70 to 700 nm and more preferably from 100 to 500 nm as determined by dynamic light scattering.

In order to prepare the suspension of step (i), the pesticide compound A, the solvent and the surfactant are mixed in any conventional mixing device which is capable of providing sufficient shear to form the desired suspension. Suitable mixing devices include in particular high shear mixers, such as Ultra-Turrax apparatus, static mixers, e.g. systems having mixing nozzles, agitator bead mills, colloid mills con mills and other homogenizers.

In general, the sequence in which the individual components are combined is not critical. However, it may be advantageous to carry step (i) out by firstly mixing the solvent and the surfactant until a homogenous mixture is obtained, and then adding the insecticide compound a) with shear to said homogenous mixture. Thus, step (i) yields a mixture of the components a), b) and c), wherein the insecticide compound A is present in the form of solid particles which are dispersed in the homogeneous phase formed by the solvent and the surfactant. Typically, the mixture of the components a), b) and c) is obtained from step (i) in the form of a slurry having a solids content in the range of from 5 to 70% by weight, particularly from 15 to 60% by weight, and more particularly from 25 to 50% by weight, based on the total weight of the slurry.

In general, the solid insecticide compound a) of formula (A) which is used in the preparation of the suspension of step (i) may be amorphous, crystalline or semicrystalline and is employed in particulate form, e.g. as a powder, as crystals, as a granulate or as a comminuted solidified melt. The particles of the solid active compound may be of regular or irregular shape, e.g. of spherical or virtually spherical form or in the form of needles. Generally, before being introduced in step (i), the solid insecticide compound particles essentially will have mean dimensions of more than 1 μm, e.g. in the range of from 1.5 to 1000 μm, particularly from 2 to 100 μm, and more particularly from 2.5 to 10 μm, as determined by dynamic light scattering.

The mixture obtained from step (i), i.e. in the form of a suspension, is subjected to suitable means for reducing the particle size of the a.i. particles present in the mixture to a particle size of less than 1 μm, frequently to a volume median diameter of not more than 0.9 μm, preferably not more than 800 nm, in particular not more 700 nm, more preferably of not more than 500 nm, e.g. from 10 to <1000 nm, frequently from 20 to 900 nm, preferably from 50 to 800 nm, in particular from 70 to 700 nm and more preferably from 100 to 500 nm, as determined by dynamic light scattering. The step (ii) may be carried out by any physical attrition method, such as grinding, crushing or milling, in particular by wet grinding or wet milling, including e.g. bead milling, hammer milling, jet milling, air classifying milling, pin milling, cryogenic grinding processes and the like.

Steps (i) and (ii) are usually performed subsequently. However it is also possible to perform these steps together.

In a preferred embodiment of the invention, step (ii) is carried out by bead milling. In particular, bead sizes in the range of from 0.05 to 5 mm, more particularly from 0.2 to 2.5 mm, and most particularly from 0.5 to 1.5 mm have been found to be suitable. In general, bead loadings in the range of from 40 to 99%, particularly from 70 to 97%, and more particularly from 65 to 95% may be used.

Step (ii) is carried out in apparatus suitable for this purpose, in particular apparatus suitable for wet grinding or wet milling methods as necessitated by the presence of the solvent b. Such apparatus are generally known. Thus, step (ii) is preferably carried out in mills, such as ball mills or bead mills, agitator ball mills, circulating mills (agitator ball mills with pin grinding system), disk mills, annular chamber mills, double cone mills, triple roll mills, batch mills, colloid mills, and media mills, such as sand mills. To dissipate the heat energy introduced during the grinding process, the grinding chambers are preferably fitted with cooling systems. Particularly suitable is the ball mill Drais Superflow DCP SF 12 from DRAISWERKE, INC. 40 Whitney Road. Mahwah, N.J. 07430 USA, a Drais Perl Mill PMC from DRAISWERKE, INC., the circulating mill system ZETA from Netzsch-Feinmahltechnik GmbH, the disk mill from Netzsch Feinmahltechnik GmbH, Seib, Germany, the bead mill Eiger Mini 50 from Eiger Machinery, Inc., 888 East Belvidere Rd., Grayslake, Ill. 60030 USA and the bead mill DYNO-Mill KDL from WA Bachofen AG, Switzerland.

The time required for reducing the particle size depends in a manner known per se on the desired grade of fineness or the desired particle size of the active compound particle and can be determined by the person skilled in the art in standard experiments. Grinding times in the range of e.g. from 1 to 48 hours have been found to be suitable, although a longer period of time is also conceivable. A grinding time of 2 to 24 hours is preferred.

The pressure and temperature conditions during comminution are generally not critical; thus, for example, atmospheric pressure has been found to be suitable. Temperatures e.g. in the range of from 10° C. to 100° C. have been found to be suitable; the chosen temperatures are usually temperatures at which the active compound a) is present as a solid.

The liquid pesticide compositions according to the invention can, after, or in particular before a formulation with additives, be converted by customary drying methods, in particular by spray-drying or freeze-drying, into powder compositions.

Before or during drying, a drying or spray auxiliary may be added. Suitable drying or spray auxiliaries for drying aqueous dispersions are known. These include protective colloids, such as polyvinyl alcohol, in particular polyvinyl alcohol having a degree of hydrolysis of >70%, carboxylated polyvinyl alcohol, phenolsulfonic acid/formaldehyde condensates, phenolsulfonic acid/urea/formaldehyde condensates, naphthalenesulfonic acid/formaldehyde condensates, naphthalenesulfonic acid/form-aldehyde/urea condensates, polyvinylpyrrolidone, copolymers of maleic acid (or maleic anhydride) and vinylaromatics such as styrene and ethoxylated derivatives thereof, copolymers of maleic acid or maleic anhydride with $C_2$-$C_{10}$-olefins, such as diisobutene, and ethoxylated derivatives thereof, cationic polymers, for example homo- and copolymers of N-alkyl-N-vinylimidazolinium compounds with N-vinyl lactams and the like, and also inorganic anti-blocking agents (sometimes also termed as anti-caking agents), such as silicic acid, in particular pyrogenic silica, alumina, calcium carbonate and the like. The drying auxiliaries are usually employed in an amount of from 0.1 to 20% by weight, based on the weight of the active compound particles in the liquid pesticide composition of the present invention.

The powder compositions obtained by drying the liquid compositions of the present invention are redispersible in water and have the same advantages as the liquid compositions. In particular the average particle size of the compound A particles in an aqueous liquid that is obtained dilution with water of such a powder composition is in the same range as given above for the liquid compositions. The powder compositions according to the invention are, like the liquid compositions, suitable for crop protection and the protection of materials, so that what is said below with regard to the use of the liquid compositions applies correspondingly also to the pulverulent compositions. Here, the powder compositions according to the invention may, depending on the area of use, be applied as such, in the form of aqueous resuspended formulations or they may be used for preparing solid formulations such as wettable powders or granules.

Solid formulations containing the powder compositions of the invention usually contain inert solid carriers. Solid carriers include, for example, mineral earths, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

As a result of aggregation processes, larger particle sizes, e.g. in the range of from 500 nm to 100 μm or up to several hundreds of micrometers, are frequently observed after the drying process has been completed. However, in general, the actual particle size is much higher, i.e. the primary particle size of the aggregated insecticide compound particles is much smaller and is in the ranges which initially have been obtained after the step (ii) has been carried out. Hence, the aggregates which have been formed upon drying are essentially broken up when being resuspended in aqueous medium, thus again yielding the desired particle sizes of less than 1 μm, frequently to a volume median diameter of not more than 0.9 μm, preferably not more than 800 nm, in particular not more 700 nm, more preferably of not more than 500 nm, e.g. from 10 to <1000 nm, frequently from 20 to 900 nm, preferably from 50 to 800 nm, in particular from 70 to 700 nm and more preferably from 100 to 500 nm, as determined by dynamic light scattering.

In general, the liquid pesticide compositions as described herein can be used for combating harmful pests including arthropod pests and nematode pests. For this purpose, the compositions may be applied as such or are preferably applied after dilution with water. Preferably, for various purposes of end user application, a so-called aqueous spray-liquor is prepared by diluting the liquid insecticide concentrate compositions of the present invention with water, e.g. tap water.

It is, however, also possible to use the liquid pesticide compositions of the present invention for preparing other formulation types and/or formulations containing active ingredients different from those of the formula A, in particular coformulations with fungicides or other insecticides.

In general, the application rate of the pure insecticide compound a) will be in the range of from 0.01 to 0.5 kg/ha, preferably from 0.05 to 0.4 kg/ha and in particular 0.1 to 0.3 kg/ha of active compound A. For application in the field, the diluted compositions (spray-liquors) are applied to e.g. plants or soils mainly by spraying, in particular foliar spraying. Application can be carried out by customary spraying techniques using, for example, water as carrier and spray liquor rates of from about 100 to 1000 l/ha (for example from 300 to 400 l/ha). Application of the preparations by the low-volume and the ultra-low-volume method is possible, as is their application in the form of microgranules.

In principle, the compositions of the present invention can be used in all areas of plant and crop protection and of the protection of materials for controlling harmful organisms or for promoting plant growth. In particular, the compositions of the invention can be employed both for protecting plants and for protecting materials against attack by such animal pests. It is also possible to treat plants and materials that have been attacked with the compositions according to the invention and to destroy the damaging organisms or at least to inhibit their growth, so that they cause no damage.

The compositions of the invention are particularly suitable in the different areas of the protection of materials against attack by animal pests. Using the compositions according to the invention, it is possible, for example, to protect cellulose-containing materials, such as wood, and also skins, hides, leather, textiles, nonwovens and the like effectively against attack by animal pests.

In general, the compositions of the invention may be applied against the following pests:

Insects from the order of the lepidopterans (Lepidoptera), for example *Agroti sypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Hellothis armigera, Hellothis virescens, Hellothis zea, Hellula undalls, Hibernia defollaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalls, Panolls flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*, beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica* 12-punctata, *Diabrotica virgifera, Epilachna varivestis, Epitrix hirtipennis, Eutinobothrus brasilensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyllopertha horticola, Phyllotreta nemorum, Phyllotreta striolata, Popillia japonica, Sitona lineatus* and *Sitophilus granaria*, dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellarla, Contarinia sorghicola, Cordylobla anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyla platura, Hypoderma lineata, Liriomyza sativae, Liriomyza trifolii, Lucilia caprina, Lucilia cuprina, Lucilia sericata, Lycoria pectoralls, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa*, thrips (Thysanoptera), e.g. *Frankliniella fusca, Frankliniella occidentalis, Frankliniella tritici, Scirtothrips citri, Thrips oryzae, Thrips palmi*and *Thrips tabaci*, hymenopterans (Hymenoptera), e.g. *Athalia rosae, Atta cephalotes, Atta sexdens, Afta texana, Hoplocampa minuta, Hoplocampa testudinea, Monomorium pharaonis, Solenopsis geminata* and *Solenopsis invicta*, heteropterans (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor*, homopterans (Homoptera), e.g. *Acyrthosiphon onobrychis, Adelges laricis, Aphidula nasturtii, Aphis fabae,*

*Aphis forbesi, Aphis pomi, Aphis gossypli, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypli, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, and Vlteus vitifolli;* termites (Isoptera), e.g. *Calotermes flavicollis, Leucotermes flavipes, Reticulitermes lucifugus* und *Termes natalensis;* orthopterans (Orthoptera), e.g. *Acheta domestica, Blatta orientalis, Blattella germanica, Forficula auricularia, Gryllotalpa gryllotalpa, Locusta migratoria, Melanoplus bivfttatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus.*

Arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma fruncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni,* Tarsonemidae spp. such as *Phytonemus pallidus* and *Polyphagotarsonemus latus;* Tenuipalpidae spp. such as *Brevipalpus phoenicis,* Tetranychidae spp. such as *Tefranychus cinnabarinus, Tefranychus kanzawai, Tefranychus pacificus, Tefranychus telarius* and *Tefranychus urticae, Panonychus ulmi, Panonychus citri,* and *oligonychus pratensis;*

Nematodes, especially plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compositions according to the invention may also be used to combat rice phatogens such as rice water weevil (*Lissorhoptrus oryzaphilus*), rice stem borer (*Chilo suppresalis*), rice leaf roller, rice leaf beetle, rice leaf miner (*Agromyca oryzae*), leafhoppers (*Nephotettix* spp.; especially smaller brown leafhopper, green rice leafhopper), planthoppers (*Delphacidae*; especially white backed planthopper, brown rice planthopper), stinkbugs.

The liquid pesticide compositions of the invention may also be applied against non-crop pests, either as such or as an aqueous dilution or as a powder composition as described above. Therefore the invention also relates to a method for controlling non-crop pests comprising contacting the pests or their food supply, habitat, breeding grounds or their locus with formulation according to the invention comprising at least a compound of the formula A.

The invention further relates to the use of a composition according to the present invention for the protection of non-living organic materials against non-crop pests.

Non-crop pests are pests of the classes Chilopoda and Diplopoda and of the orders Isoptera, Diptera, Blattaria (Blattodea), Dermaptera, Hemiptera, Hymenoptera, Orthoptera, Siphonaptera, Thysanura, Phthiraptera, Araneida, Parasitiformes and Acaridida, for example:

centipedes (Chilopoda), e.g. *Scutigera coleoptrata,* millipedes (Diplopoda), e.g. *Narceus* spp., spiders (Araneida), e.g. *Lafrodectus mactans,* and *Loxosceles reclusa,* scabies (Acaridida): e.g. *sarcoptes* sp, ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabills, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae,* termites (Isoptera), e.g. *Calotermes flavicollis, Leucotermes flavipes, Heterotermes aureus, Reticulitermes flavipes, Reticulitermes virginicus, Reticulitermes lucifugus, Termes natalensis,* and *Coptotermes formosanus,* cockroaches (Blattaria—Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis,* flies, mosquitoes (Diptera), e.g. *Aedes aegypti, Aedes albopictus, Aedes vexans, Anastrepha ludens, Anopheles maculipennis, Anopheles crucians, Anopheles*

*albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyla hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vfttatum, Stomoxys calcitrans, Tabanus bovinus, Tabanus atratus, Tabanus lineola*, and *Tabanus similis,*

Earwigs (Dermaptera), e.g. *forficula auricularia,* true bugs (Hemiptera), e.g. *Cimexlectularius, Cimexhemipterus, Reduvius senilis, Triatoma* spp., *Rhodnius prolixus*, and *Arilus critatus,* ants, bees, wasps, sawflies (Hymenoptera), e.g. *Crematogaster* spp., *Hoplocampa minuta, Hoplocampa testudinea, Monomorium pharaonis, Solenopsis geminata, Solenopsis invicta, Solenopsis richteri, Solenopsis xyloni, Pogonomyrmex barbatus, Pogonomyrmex calfornicus, Dasymutilla occidentalis, Bombus* spp. *Vespula squamosa, Paravespula vulgaris, Paravespula pennsylvanica, Paravespula germanica, Dolichovespula maculata, Vespa crabro, Pollstes rubiginosa, Camponotus floridanus,* and *Linepithema humile,* crickets, grasshoppers, locusts (Orthoptera), e.g. *Acheta domestics, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalna,* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

For example, compositions according to the invention can be used for the protection of non-living organic materials, including but are not limited to house-hold goods, such as fats, oils, mono- oligo- or polyorganosaccharides, proteins, or fresh or decaying fruits; cellulose-containing materials, e.g. wooden materials, such as houses, trees, board fences, or sleepers and also paper; and also construction materials, furniture, leathers, animal, plant and synthetic fibers, vinyl articles, electric wires and cables as well as styrene foams.

Furthermore, a composition according to the invention can be used for the protection of non-living organic materials against non-crop pests selected from the group consisting of the class Diplopoda and of the orders Isoptera, Diptera, Blattaria (Blattodea), Dermaptera, Hemiptera, Hymenoptera, Orthoptera, and Thysanura.

The present invention also relates to a method for the protection of non-living organic materials against non-crop pests as mentioned above comprising contacting the pests or their food supply, habitat, breeding grounds, their locus or the non-living organic materials themselves with an pesticidally effective amount of a composition according to the invention.

Furthermore, a composition according to the invention can be used for protecting cellulose-containing non-living organic materials, e.g. for protecting cellulose-containing non-living organic materials against non-crop pests from the Isoptera, Diptera, Blattaria (Blattodea), Hymenoptera, and Orthoptera orders, most preferably the Isoptera orders.

The present invention also provides a method for protecting cellulose-containing non-living organic materials against non-crop pests, preferably from the Isoptera, Diptera, Blattaria (Blattodea), Hymenoptera, and Orthoptera orders, most preferably the Isoptera orders, comprising contacting the pests or their food supply, habitat, breeding grounds, their locus or the cellulose-containing non-living organic materials themselves with a composition according to the invention.

Furthermore, a composition according to the invention can be used for for protecting mono- oligo- or polysaccharides and proteins.

Furthermore, a composition according to the invention can be used for protection of mono- oligo- or polysaccharides and proteins against non-crop pests selected from the Dermaptera, Diplopoda, Isoptera, Diptera, Blattaria (Blattodea), Hymenoptera, Orthoptera and Tysanura orders, most preferably the Isoptera, Diptera, Blattaria (Blattodea), and Hymenoptra orders.

Furthermore, a composition according to the invention can be used for used for protection of animals against non-crop pest of the class Chilopoda, and of the orders Araneida, Hemiptera, Diptera, Phthiraptera, Siphonaptera, Parasitiformes and Acaridida by treatment of the pests in water bodies and/or in and around buildings, including but not limited to walls, ground, manure piles, turf grass, pastures, sewers and materials used in the construction of buildings and also mattresses and bedding, with a formulation according to the present invention.

Animals include warm-blooded animals, including humans and fish. Thus, a formulation according to the invention can be used for protection of warm-blooded animals, such as cattle, sheep, swine, camels, deer, horses, poultry, rabbits, goats, dogs and cats.

Furthermore, a composition according to the invention can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). A formulation according to the invention can be applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant control composition of the present invention is directly applied to the nest of the ants or to its surrounding or via bait contact.

Furthermore, a composition according to the invention can be applied preventively to places at which occurrence of the pests is expected.

The invention furthermore comprises seeds treated with the formulation according to the present invention.

Suitable seeds are for example various crop seeds, fruit species, vegetables, spices and ornamental seed, for example corn/maize (sweet and field), durum wheat, soybean, wheat, barley, oats, rye, triticale, bananas, rice, cotton, sunflower, potatoes, pasture, alfalfa, grasses, turf, sorghum, rapeseed, Brassica spp., sugar beet, eggplants, tomato, lettuce, iceberg lettuce, pepper, cucumber, squash, melon, bean, dry-beans, peas, leek, garlic, onion, cabbage, carrot, tuber such as sugar cane, tobacco, coffee, turf and forage, cruciferous, cucurbits, grapevines, pepper, fodder beet, oil seed rape, pansy, impatiens, petunia and geranium.

The following examples are intended to further illustrate the present invention without limiting its scope in any way.

I. Analytics:

Particle sizes were determined by dynamic light scattering with a Malvern Mastersizer 2000 system at 25° C. All particle sizes cited herein are volume average particle diameters d(0.5) or d(v, 0.5).

II. Ingredients:

Surfactant 1: 32% by weight aqueous solution of graftcopolymer based on methyl methacrylate and polyethylene oxide—Atlox® 4913 (Uniqema)

Surfactant 2: Sodium salt of a naphthalene sulfonic acid formaldehyde condensate—Morwet® D425 (Akzo Nobel)

Surfactant 3: Ethoxylated Tristyrylphenol—Soprophor®BSU (Rhodia)

Surfactant 4: Blockcopolymer of ethylene oxide and propylene oxide, $M_N$ 6500, EO/PO ratio 50:50—Pluronic® P105 (BASF AG)

Surfactant 5: Blockcopolymer of ethylene oxide and propylene oxide, $M_N$ 7700, EO/PO ratio 60:40—Pluraflo® 1060 (BASF AG)

Surfactant 6: copolymer of styrene and acrylic acid—Atlox® Metasperse 500 L (Uniqema)

Surfactant 7: mixture of alkyl naphthalene sulfonic acid sodium salt and sodium salt of dioctylsulfosuccinat—Morwet® EFW (Akzo Nobel)

Surfactant 8: $C_1$-$C_9$-alkylether of poly-$C_2$-$C_3$-alkylene glycol ($M_N$ 2900)—Atlox® G5000 (Uniqema)

Surfactant 9: Sodium salt of dioctylsulfosuccinat—Aerosol®OTB (Cytec)

III. Preparation of the compositions of the invention:

EXAMPLE 1

Into 55 g of water, 3 g of surfactant 1 and 2 g of surfactant 8 were dissolved and then mixed until a homogenous phase was obtained. Then, 40 g of metaflumizone were added and dispersed using a high shear mixer. A slurry having a solids content of about 40% by weight was obtained. The slurry was then passed through a bead mill (Eiger Mini 50) using 0.8 mm beads with a bead loading of 90% until a particle size of 0.8 μm was achieved.

EXAMPLE 2

Into 40 kg of water, 10 kg of propylene glycol, and 5 kg of surfactant 2 were dissolved and then mixed until a homogenous phase was obtained. Then, 45 kg of metaflumizone have been added and dispersed using a high shear mixer. A slurry having a solids content of about 45% by weight was obtained. The slurry was passed through a 5 liter bead mill (Drais) using 1.0 mm bead with a bead loading of 70% until a particle size of 0.7 μm was achieved.

EXAMPLE 3

Into 55 g of water, 7 g of ethylene glycol, 5 g of surfactant 2, and 3 g of surfactant 4 were dissolved and then mixed until a homogenous phase was obtained. Then, 30 g of metaflumizone were added and dispersed using a high shear mixer. A slurry having a solids content of about 30% by weight was obtained. The slurry was passed through a bead mill (Dynomill) using 0.8 mm bead with a bead loading of 80% until a particle size of 0.8 μm was achieved.

EXAMPLE 4

Into 38.8 kg of water, 3.37 kg of surfactant 3, 1.1 kg of surfactant 5, and 2.72 kg of surfactant 9 were dissolved and then mixed until a homogenous phase has been obtained. Then, 25 kg of metaflumizone were added and dispersed using a high shear mixer. A slurry having a solids content of about 35.3% by weight was obtained. The slurry was passed through a Drais 5 liter bead mill using 0.8 mm bead with a bead loading of 70%. Samples were removed after 0.5, 4 and 13 hours, respectively, of bead milling, yielding particle sizes of about 2.44 μm, 0.71 μm and 0.26 μm, respectively.

EXAMPLES 5

According to the process described in example 1 the following pesticide compositions were prepared by applying different milling times. The compositions had the following overall composition:

34% by weight of metaflumizone (purity 97%);
5.2% by weight of surfactant 3;
1.7% by weight of surfactant 5;
4.3% by weight of surfactant 9;
49% by weight of water and
5.8% by weight of propylene glycol.

Samples were removed after different milling times, respectively, of bead milling, yielding particle sizes of about 1.0 μm, 0.70 μm and 0.20 μm, respectively.

IV. Chemical Stability

Liquid insecticide concentrate compositions obtained according to the method of example 4 have been stored at 20° C. and 30° C., respectively, for a period of 24 months. The chemical stability has been assessed by measuring the respective particle sizes at distinct time intervals. The data obtained is listed in table 2, wherein particle sizes are given as volume median diameter in [μm].

TABLE 2*

| Storage temperature | initial | 3 m | 6 m | 9 m | 12 m | 18 m | 24 m |
| --- | --- | --- | --- | --- | --- | --- | --- |
| 20° C. | 0.25 | 0.24 | 0.24 | 0.24 | 0.24 | 0.25 | 0.25 |
| 30° C. | 0.25 | na | na | na | 0.24 | na | 0.25 |

*particle sizes in [μm]; na = not assessed; m = months

Since the particle sizes observed essentially remain unaltered over storage time, the liquid insecticide concentrate compositions of the present invention have good chemical stability properties.

V. Biological Activity

The lethal concentrations $LC_{50}$ and $LC_{90}$ have been determined by evaluating the performance of the liquid insecticide concentrate compositions of the present invention against Southern Armyworm (*Spodoptera eridania*), third instar. A stock composition of the composition obtained from examples 4 or 5, respectively, was diluted into a container of water. Lima bean leaves were dipped into the thus prepared dilution and allowed to air-dry. A single treated leaf was each placed topside-up onto water-moistened filter paper in multiple plastic petri dishes. Seven larvae were placed onto each leaf, and then each arena was sealed with petri dish covers. Each treatment was replicated 4-fold (1 replicate=1 petri dish arena) with 7 insects. Following treatment application, infested plants were held in the laboratory under fluorescent lighting and at a constant temperature of 26° C. Larval mortality/morbidity (i.e. number of dead larvae/number of larvae tested) was assessed at 5 days post-treatment.

Table 3 lists the larval mortality/morbidity data which have been obtained for various concentrations of a.i. applied and which have resulted from using compositions of example 4 having different mean particle sizes.

TABLE 3

Results for the compositions of example 4

| Concentration of a.i. applied [ppm] | Larval mortality/morbidity* [%] | | |
|---|---|---|---|
| | d(0.5) = 2.44 µm | d(0.5) = 0.71 µm | d(0.5) = 0.26 µm |
| 10.0 | 100.0 | 100.0 | 100.0 |
| 6.0 | 92.9 | 100.0 | 100.0 |
| 3.0 | 0.0 | 75.0 | 96.4 |
| 1.0 | 0.0 | 0.0 | 17.9 |
| 0.3 | 0.0 | 0.0 | 0.0 |
| 0.1 | 0.0 | 0.0 | 0.0 |

*number of dead larvae/number of larvae tested

The mortality levels based on the number of life larvae. From this data, the $LC_{50}$ and $LC_{50}$ values for each composition have been estimated via Log Dose-Probit analysis. The data obtained are summarized in table 4.

TABLE 4

Results for the compositions of example 4

| Lethal Concentration Rates (LC) | Larval mortality/morbidity | | |
|---|---|---|---|
| | d(0.5) = 2.44 µm | d(0.5) = 0.71 µm | d(0.5) = 0.26 µm |
| $LC_{50}$ | 4.40 | 2.20 | 1.50 |
| Biological benefit* | 1 | 2 | 2.9 |
| $LC_{90}$ | 5.8 | 3.75 | 2.46 |
| Biological benefit* | 1 | 1.5 | 2.4 |

*The biological benefit is the ratio of the LC values of the d(0.5) = 2.44 µm size sample (control, i.e. standard or typical SC) to the LC values of the d(0.5) = 0.71 µm and d(0.5) = 0.26 µm size sample, respectively.

Since the $LC_{50}$ and $LC_{90}$ for the samples having a d(0.5) of less than 1 µm are much lower than the d(0.5)=2.44 µm size control sample, the biological benefit is increased significantly, namely by a factor in the range of from at least 1.5 to up to 2.9.

Similarly, mortality/morbidity data have been determined for various concentrations of a.i. applied by using compositions of example 5 having different mean particle sizes. From these data, the $LC_{50}$ and $LC_{90}$ values for each composition have been estimated via Log Dose-Probit analysis. The data obtained are summarized in tables 5 and 6.

TABLE 5

Results for the compositions of example 5

| Concentration of a.i. applied [ppm] | Larval mortality/morbidity* [%] | | |
|---|---|---|---|
| | d(0.5) = 1.0 µm | d(0.5) = 0.7 µm | d(0.5) = 0.2 µm |
| 10.0 | 100.0 | 100.0 | 100.0 |
| 6.0 | 96.4 | 100.0 | 100.0 |
| 3.0 | 60.7 | 100.0 | 100.0 |
| 1.0 | 7.1 | 46.4 | 35.7 |
| 0.3 | 0.0 | 10.7 | 10.7 |
| 0.1 | 0.0 | 7.1 | 0.0 |

*number of dead larvae/number of larvae tested

TABLE 6

Results for the compositions of example 5

| Lethal Concentration Rates (LC) | d(0.5) = 1.0 µm | d(0.5) = 0.7 µm | d(0.5) = 0.2 µm |
|---|---|---|---|
| $LC_{50}$ | 2.41 | 0.79 | 0.98 |
| Biological benefit* | 1 | 3.1 | 2.5 |
| $LC_{90}$ | 4.88 | 2.78 | 2.47 |
| Biological benefit* | 1 | 1.8 | 2.0 |

*The biological benefit is the ratio of the LC values of the d(0.5) = 1 µm size sample (control) to the LC values of the d(0.5) = 0.7 µm and d(0.5) = 0.2 µm size sample, respectively.

We claim:

1. A liquid pesticide concentrate composition, which comprises:

a) 5 to 60% by weight, based on the total weight of the concentrate composition, of a pesticide compound of the formula A (A)

[chemical structure showing urea compound with hydrazone linkage, bearing substituents $R^{11}$, $R^{12}$, $R^{13}$ on three phenyl rings]

wherein $R^{11}$ and $R^{12}$ are each independently hydrogen, halogen, CN, $C_1$-$C_4$ alkyl, $C_1$-$C_4$ alkoxy, $C_1$-$C_4$ haloalkyl or $C_1$-$C_4$ haloalkoxy and $R^{13}$ is $C_1$-$C_4$ alkoxy, $C_1$-$C_4$ haloalkyl or $C_1$-$C_4$ haloalkoxy, or an agriculturally acceptable salt thereof;

b) from 30 to 94.9% by weight, based on the total weight of the concentrate composition, a solvent selected from the group consisting of water and mixtures of water with polyhydric $C_2$-$C_4$ alcohols, wherein the pesticide compound of the formula A is soluble in the solvent in an amount of not more than 2 g/l at 25° C./1013 mbar, where in the weight ratio of water to polyhydric alcohol is in the range of from 50:1 to 2:1; and c) from 0.1 to 20% by weight, based on the total weight of the concentrate composition, of one or more surfactants;

wherein the compound of the formula A is present in the form of particles that are dispersed in the mixture of solvent and surfactant and that have a volume median diameter, as determined by dynamic light scattering, of not more than 0.9 µm, wherein the pesticide compound of the formula A is 2-[2-(4-cyanophenyl)-1-[3-(trifluoromethyl)-phenyl]ethylidene]-N-[4-(trifluoromethoxy)phenyl]hydrazinecarboxamide and wherein the particles of the pesticide compound of the formula A have a volume median diameter, as determined by dynamic light scattering, in the range from 20 to 900 nm.

2. The composition of claim 1, wherein the weight ratio of the compound of formula A to the surfactant is in the range of from 2:1 to 20:1.

3. The composition of claim 1, wherein the solvent is a mixture of water and a polyhydric $C_2$-$C_4$ alcohol that is selected from the group consisting of ethylene glycol, 1,2-propane diol, 1,3-propane diol, glycerol and 1,4-butane diol, where the weight ratio of water to polyhydric alcohol is in the range of from 99:1 to 1:1.

4. The composition of claim 1, wherein the solvent comprises at least 99% by weight of water, based on the total weight of the solvent present in the composition.

5. The composition of claim 1, wherein the surfactant comprises at least one anionic surfactant.

6. The composition of claim 1, wherein the surfactant comprises at least one non-ionic surfactant.

7. The composition of claim 1, wherein the surfactant comprises at least one polymeric surfactant.

8. The composition of claim 1, wherein the particles of the pesticide compound of the formula A have a volume median diameter, as determined by dynamic light scattering, in the range from 50 to 800 nm.

9. The composition of claim 8, wherein the particles of the pesticide compound of the formula A have a volume median diameter, as determined by dynamic light scattering, in the range from 100 to 500 nm.

10. A process for preparing the composition of claim 1, comprising:
(i) preparing a suspension of the compound of formula A in a mixture of the solvent and the surfactant, wherein the compound of formula A is present in the form of particles; and
(ii) reducing the particle size of the compound of formula A present in the suspension of step (i) to a volume median diameter of from 20 to 900 nm, as determined by dynamic light scattering.

11. The process of claim 10, wherein step (i) comprises mixing the solvent and the surfactant until a homogenous mixture is obtained, adding the compound of formula A to said homogenous mixture and applying shear to the mixture containing the compound of formula A.

12. The process of claim 10, wherein step (ii) comprises subjecting the suspension of step (i) to milling.

13. A powder composition obtained by drying the liquid pesticide composition of claim 1.

14. An aqueous composition in the form of a spray liquor, obtained by dilution with water of the liquid composition of claim 1.

15. An aqueous composition in the form of a spray liquor, obtained by dilution with water of the powder composition of claim 13.

16. A method of combating harmful organisms selected from the group consisting of arthropod and nematode pests, which comprises applying the composition of claim 1 to said harmful organisms, their habit, breeding ground, food supply, plant, seed, soil, area, material or environment in which the harmful organisms are growing or may grow, or to the materials, plants, seeds, soils, surfaces or spaces to be protected from attack or infestation by harmful organisms.

17. A method for protecting crops from attack or infestation by harmful organisms selected from the group consisting of arthropod and nematode pests which comprises applying the spray liquor of claim 14 to a crop plant.

18. A method for protecting seeds from attack or infestation by harmful organisms selected from the group consisting of arthropod and nematode pests, which comprises applying the composition of claim 1 to a seed.

19. The composition of claim 1, wherein the weight ratio of water to polyhydric alcohol is in the range of from 40:1 to 10:1.

20. The composition of claim 1, wherein the insecticide compound of the formula A is soluble in the solvent in an amount of not more than less than 0.2 g/l at 25° C./1013 mbar.

21. The composition of claim 1, wherein the compound of the formula A is present in the form of particles that are dispersed in the mixture of solvent and surfactant and that have a volume median diameter, as determined by dynamic light scattering, of not more than 800 nm.

* * * * *